(12) United States Patent
Takami et al.

(10) Patent No.: US 7,799,090 B2
(45) Date of Patent: Sep. 21, 2010

(54) MODULARIZED PROSTHESIS LEG COVER

(75) Inventors: Kenji Takami, Nagoya (JP); Takashi Aoyama, Nagoya (JP); Mitsuru Hayashi, Komaki (JP); Takuya Miyagawa, Komaki (JP); Masaya Akutagawa, Inuyama (JP); Mitsuhisa Suzuki, Inuyama (JP)

(73) Assignees: Matsumoto P&O Co., Ltd., Nagoya-shi (JP); Imasen Engineering Corporation, Inuyama-shi (JP)

( * ) Notice: Subject to any disclaimer, the term of this patent is extended or adjusted under 35 U.S.C. 154(b) by 391 days.

(21) Appl. No.: 11/682,501

(22) Filed: Mar. 6, 2007

(65) Prior Publication Data

US 2007/0150069 A1 Jun. 28, 2007

(51) Int. Cl.
*A61F 2/74* (2006.01)
(52) U.S. Cl. ........................................................ 623/27
(58) Field of Classification Search .................. 623/27, 623/32–36, 38; 602/62; *A61F 2/60, 2/72*
See application file for complete search history.

(56) References Cited

U.S. PATENT DOCUMENTS

| | | | | |
|---|---|---|---|---|
| 26,753 A | * | 1/1860 | Douglass | 623/39 |
| 35,723 A | * | 6/1862 | White | 623/33 |
| 1,316,347 A | * | 9/1919 | Bidou | 623/46 |
| 3,111,683 A | * | 11/1963 | Bach | 623/38 |
| 4,463,459 A | * | 8/1984 | Shorter et al. | 623/47 |
| 5,880,964 A | * | 3/1999 | Schall et al. | 700/159 |

FOREIGN PATENT DOCUMENTS

| | | |
|---|---|---|
| DE | 43 27 352 C1 | 4/1995 |
| JP | 5-51319 | 7/1993 |
| JP | 6-225897 | 8/1994 |
| JP | 3103785 | 6/2004 |

* cited by examiner

*Primary Examiner*—William H. Matthews
*Assistant Examiner*—Marcia Hoffman
(74) *Attorney, Agent, or Firm*—Oblon, Spivak, McClelland, Maier & Neustadt, L.L.P.

(57) ABSTRACT

A modularized prosthesis leg cover quickly covers a prosthesis leg and does not affect bending or stretching motion of a knee joint part of the prosthesis leg, thus preventing damage to the knee joint part of the prosthesis leg. Thus, the modularized prosthesis leg cover includes a thigh module, which can be mounted to a thigh socket of the prosthesis leg, a lower leg module, which can be fastened to a calf pipe of the prosthesis leg, and a patella module, which can be rotatably assembled with the lower leg module. The prosthesis leg cover, which is formed by assembling the modules, is covered with a skin module, which is made of a stretchable fiber. The respective modules are provided as prefabricated modules. A method of manufacturing the prosthesis leg cover is also provided.

3 Claims, 18 Drawing Sheets

MODULARIZED PROSTHESIS LEG COVER

BACKGROUND OF THE INVENTION

1. Field of the Invention

The present invention relates, in general, to prosthesis legs and, more particularly, to a cover for endoskeletal prosthesis legs.

2. Description of the Related Art

Generally, endoskeletal prosthesis legs have been preferably used because they having many functional advantages. In conventional endoskeletal prosthesis legs, the skeletons of the prosthesis legs are important functional parts, so that a shell or a cover for covering a prosthesis leg is required. In the related art, to provide a shell or a cover for covering the endoskeletal prosthesis leg, a cylindrical urethane foam block is cut to form the thigh part or the calf part of a lower leg part. Of course, the thigh parts or the calf parts of conventional prosthesis leg covers must be specifically produced as integral one-piece parts to fit patients. The conventional soft and one-piece prosthesis leg covers made of urethane foam are disadvantageous as follows. 1) The kneecap is repeatedly expanded and contracted, thus becoming damaged within a short period of time. 2) The conventional soft and one-piece prosthesis leg covers do not have a symmetrical cylindrical shape, so that it is very difficult to cut them. 3) When the knee joint part of the prosthesis leg is bent, the cover is expanded, so that the knee joint part is overloaded. Particularly, while a patient, wearing the conventional prosthesis leg cover, swings his/her prosthesis leg, the prosthesis leg cover hinders the functionality of the knee joint part.

Japanese Patent Laid-open Publication No. Hei. 6-225897 proposed a prosthesis leg soft foam cover, which uses both a patella part and a patellar landing guide, and is configured to avoid overload-induced deformation of the soft foam cover while executing bending motion of the knee joint part, thus avoiding damage to the soft foam cover and maintaining a desired appearance of the soft foam cover. Further, Japanese Utility Model Registration No. 3103785 proposed a prosthesis leg foam cover, which comprises two pieces that are an upper leg shell and a lower leg shell, with both an elastic band installed between the upper and lower leg shells, and a patella pad provided in back of the elastic band, thus improving the appearance of a knee joint part when a patient wearing the prosthesis leg foam cover, sits on a chair.

However, the conventional foam covers for covering the prosthesis legs are specific products, which must be cut to fit patients. Thus, the conventional foam covers for covering the prosthesis legs take a long time to produce and are thus very expensive.

SUMMARY OF THE INVENTION

Accordingly, the present invention has been made keeping in mind the above problems occurring in the related art, and an object of the present invention is to provide a modularized prosthesis leg cover, which can be fabricated to comprise a plurality of modules and covers a prosthesis leg, thus providing a prosthesis leg having an improved appearance similar to the appearance of a real leg, and which can cover a prosthesis leg using an assembly of prefabricated modules.

The modularized prosthesis leg cover of the present invention is advantageous compared to conventional prosthesis leg covers made of foam for the following reasons. 1) The modularized prosthesis leg cover can be easily produced. 2) The modularized prosthesis leg cover can quickly cover a prosthesis leg after quickly assembling prefabricated modules with each other to form the prosthesis leg cover. 3) The modularized prosthesis leg cover can cover a prosthesis leg without being limited by the shapes or kinds of parts of the prosthesis leg, so that the modularized prosthesis leg cover has wide applicability. 4) The modularized prosthesis leg cover can avoid damage, degradation, deformation or breakage, thus having high durability. 5) The appearance of the modularized prosthesis leg cover is similar to the appearance of a real leg. Particularly, when the knee joint part is bent, the appearance of the modularized prosthesis leg cover is natural. 6) The modularized prosthesis leg cover is light, thus having high practical utility. 7) The modularized prosthesis leg cover does not affect bending motion of the knee joint part, which is an important skeletal part of the prosthesis leg.

In order to achieve the above object, according to the first aspect of the present invention, there is provided a modularized prosthesis leg cover, comprising: a thigh module, which is mounted to a predetermined portion of a prosthesis leg at a position above a knee joint part and forms a thigh shell of the prosthesis leg; a patella module, which forms a kneecap of the prosthesis leg; and a lower leg module, which comprises: a tibia crest part that is mounted to a predetermined portion of the prosthesis leg at a position below the knee joint part and forms a tibia crest; and a calf part that forms a calf and has a part that is more flexible than the tibia crest part. In the above case, the portion of the prosthesis leg that is above the knee joint part and to which the thigh module is mounted may be a thigh socket of the prosthesis leg. Further, the portion of the prosthesis leg that is below the knee joint part and to which the tibia crest part of the lower leg module is mounted may be a calf pipe of the prosthesis leg.

Due to the above-mentioned construction of the present invention, a desired shell of the prosthesis leg can be fabricated with the three modules, which are the thigh module, the patella module, and the lower leg module. Thus, when only limited kinds of parts of the modules are marketed as prefabricated parts such that different sizes and shapes can be made available for each part, some suitable parts can be selected from among the prefabricated parts according to the characteristics of a patient, and are assembled with each other, thus forming respective modules. Thereafter, the modules are assembled together to form a desired prosthesis leg cover that fits the patient. Further, when the patient bends and stretches the knee joint part of the prosthesis leg, the modules do not interfere with each other, so that the bending motion of the knee joint part, which is the most important skeletal part of the prosthesis leg, is not obstructed. Further, the respective modules of the prosthesis leg avoid damage, degradation or deformation despite undergoing repeated bending motions.

According to the second aspect of the present invention, the modularized prosthesis leg cover may further comprise: a skin module, which comprises contractible tights covering the thigh module, the patella module and the lower leg module. When the three modules are covered with the skin module, the appearance of the prosthesis leg cover can be improved, so that the prosthesis leg cover takes on a shape similar to that of a real leg. Further, when the prosthesis leg cover is covered with the skin module, the skin module provides a smooth surface, as if the prosthesis leg cover were wearing a stocking, so that it is easy for a patient to put on or take off garments such as trousers. The skin module is made of a stretchable fiber, thus having high elasticity and reduced resistance to expansion and contraction, so that the skin module does not affect the bending or stretching motion of the knee joint part, which is the most important skeletal part of the prosthesis leg.

According to the third aspect of the present invention, the patella module of the modularized prosthesis leg cover may comprise: a first stay part, which extends upwards and backwards from the upper end of the tibia crest part mounted to the prosthesis leg at the position below the knee joint part; a stay shaft provided on the upper end of the first stay part, such that the stay shaft is located at a predetermined position, which is adjacent to and lower than the knee joint part of the prosthesis leg; a second stay part, which is rotatably mounted to the first stay part by the stay shaft and extends upwards and forwards; and a patella part mounted to an end of the second stay part.

Due to the above-mentioned construction of the patella module, the position of the patella part can be appropriately adjusted by controlling the rotated position of the second stay part around the stay shaft. Further, because the stay shaft, around which the patella part is rotated, is located at a position that is lower than the knee joint part, when the knee joint part is bent, the patella part is moved slightly backwards. Thus, the motion of the patella part is similar to the motion of the patella of a real leg, and thus the location and appearance of the bent knee joint part of the prosthesis leg are similar to those of a real leg.

According to the fourth aspect of the present invention, the skin module of the modularized prosthesis leg cover may comprise a support for supporting the patella part at a position corresponding to the kneecap. The support for supporting the patella part may comprise an inside pocket, which is provided inside the skin module. Due to the above-mentioned skin module having the support, the patella module may comprise only the patella part (or the patella part added with bands). Thus, the patella module does not require many parts, such as stays, so that the prosthesis leg cover can be fabricated with a reduced number of parts, and thus productivity is increased. Further, the prosthesis leg cover can be easily produced. Further, a variety of knee joint parts can be used with the patella module without limit. The patella module can be easily and simply changed with a new one. Further, when the patella module is provided with upper and lower bands, it is possible to reliably prevent the undesired leftward and rightward movement of the patella module.

According to the fifth aspect of the present invention, the calf part of the lower leg module may comprise: a muscular coleus pad corresponding to a muscular soleus; and a muscular gastrocnemius pad corresponding to a muscular gastrocnemius. Due to the above-mentioned construction of the calf part, it is possible to easily and simply provide many patients with calf parts similar to the calf of a real leg.

According to the sixth aspect of the present invention, there is provided a modularized prosthesis leg cover, comprising: a thigh module, which is mounted to a prosthesis leg at a position above a knee joint part and forms a thigh shell of the prosthesis leg; a patella module, which forms a kneecap of the prosthesis leg; a lower leg module, which is mounted to the prosthesis leg at a position below the knee joint part and forms a lower leg part of the prosthesis leg; a lower leg front pad and a lower leg rear pad, which are mounted to the lower leg module and form a lower leg shell; and a skin module, which covers the thigh module, the patella module, the lower leg front pad, and the lower leg rear pad. Thus, it is easy to provide a prosthesis leg cover that fits a patient by assembling the modules.

According to the seventh aspect of the present invention, the lower leg module may comprise a longitudinal guide slit for guiding movement of the patella module. Due to the longitudinal guide slit, it is possible to precisely guide the movement of the patella module in response to bending motion of the knee joint part.

According to the eighth aspect of the present invention, the skin module may be provided with a reversed U-shaped knitted part, which has high contractibility, at a position corresponding to the kneecap. Due to the reverse U-shaped knitted part of the skin module, it is possible to control the movement of the patella module in response to the bending motion of the knee joint part.

According to the ninth aspect of the present invention, there is provided a method for manufacturing a modularized prosthesis leg cover, comprising; designing a plurality of modules, which are obtained by grouping parts of the prosthesis leg cover into a plurality of groups, each comprising a plurality of associated parts, and producing the modules; and assembling the produced modules with each other, thus forming a prosthesis leg cover. When the prosthesis leg cover is designed and produced as a modularized system, as described above, modules that fit a patient can be easily manufactured. Further, a desired prosthesis leg cover, which fits a patient, can be quickly provided by selecting suitable modules from among prefabricated modules and assembling the selected modules with each other to form a prosthesis leg cover. In other words, a variety of prosthesis leg covers, which fit different patients and thus have different shapes and sizes, can be efficiently and quickly provided.

BRIEF DESCRIPTION OF THE DRAWINGS

The above and other objects and features of the present invention will become apparent from the following description of a preferred embodiment thereof, given in conjunction with the accompanying drawings, in which.

DETAILED DESCRIPTION OF THE INVENTION

Various embodiments of the present invention will now be described in detail with reference to the accompanying drawings.

Figure 1:
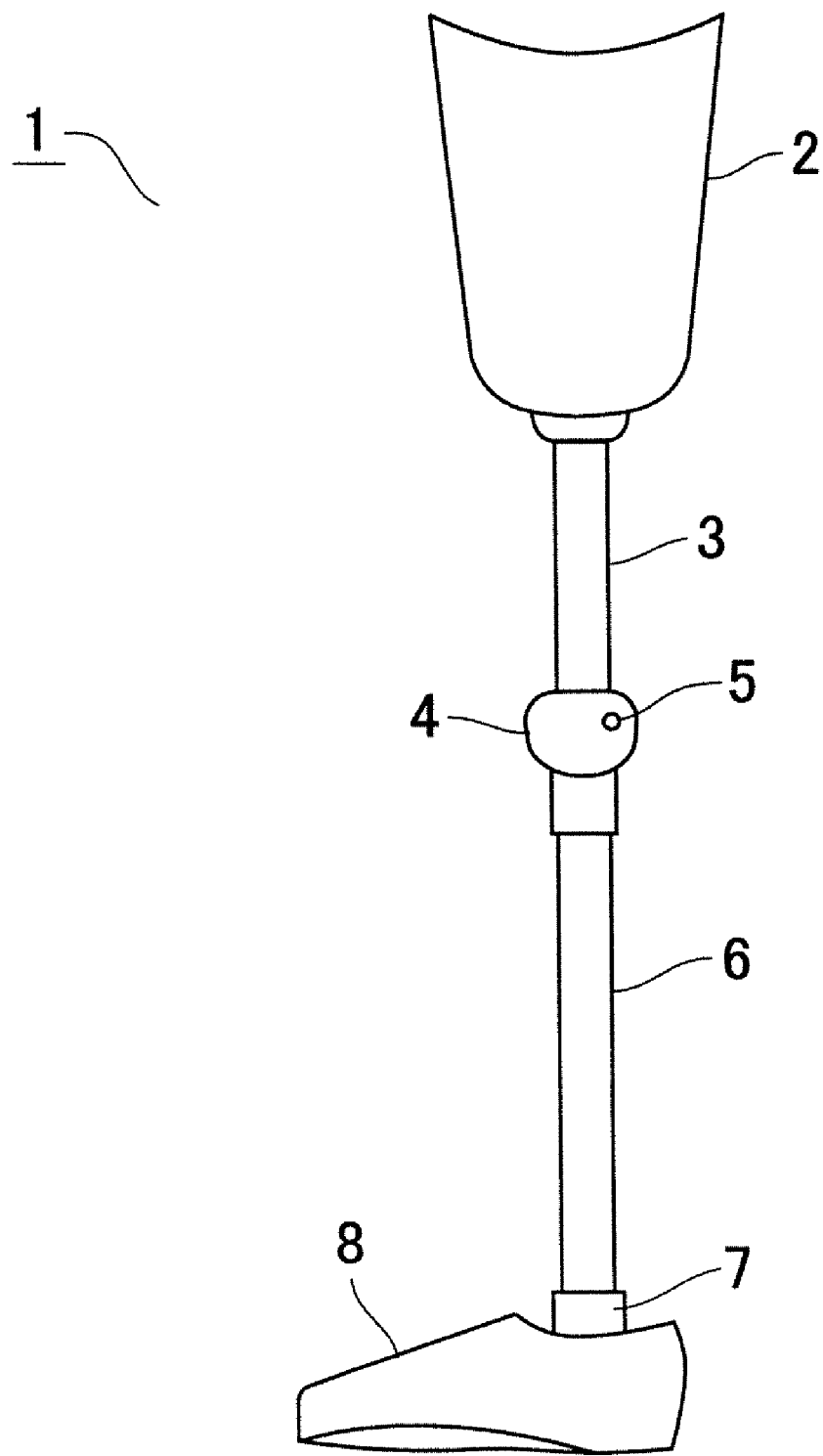
FIG. 1 is a side view illustrating an endoskeletal prosthesis leg of the present invention.

FIG. 1 is a side view illustrating an endoskeletal prosthesis leg 1 of the present invention. As shown in the drawing, the endoskeletal prosthesis leg 1 comprises a thigh socket 2, which is fitted over the stump of a patient; a thigh pipe 3; a knee joint module 4; a lower leg pipe 6; an ankle joint module 7; and a foot part 8. The knee joint module 4 includes a knee joint shaft 5. The patient, wearing the prosthesis leg 1, can efficiently walk, but he/she may want to improve the appearance of the prosthesis leg 1, and thus the prosthesis leg cover of the present invention is preferably used.

Figure 2:
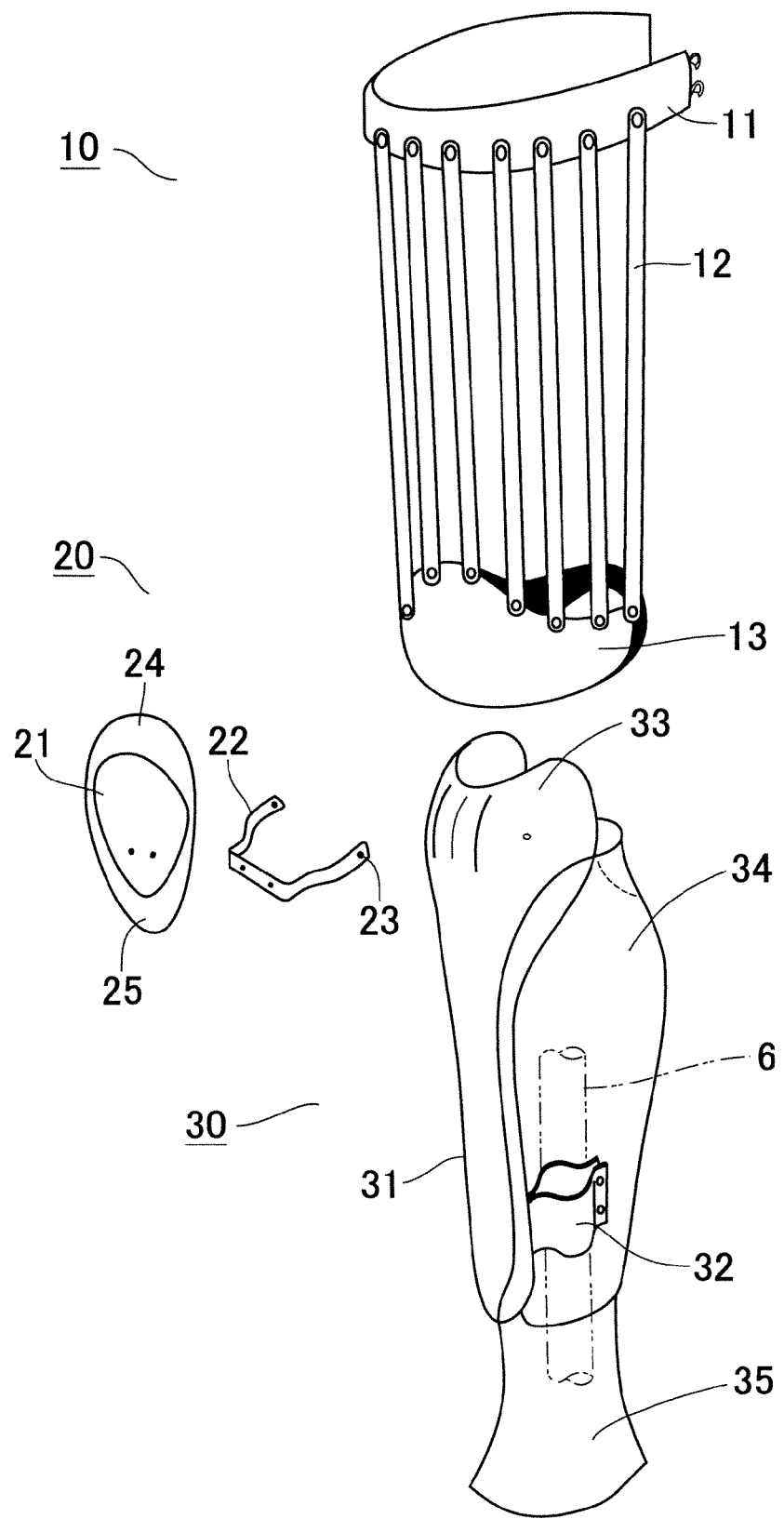
FIG. 2 is an exploded perspective view illustrating parts of a modularized prosthesis leg cover according to a first embodiment of the present invention.

FIG. 2 is an exploded perspective view illustrating parts of the modularized prosthesis leg cover according to a first embodiment of the present invention. As shown in the drawing, the prosthesis leg cover comprises: a thigh module 10, which is mounted to the thigh socket 2 and surrounds the thigh 2; a patella module 20, and a lower leg module 30, which is mounted to the lower leg pipe 6 and surrounds the lower leg pipe 6. The thigh module 10 comprises: a proximal annular band 11, which surrounds the proximal part of the thigh of the patient; a plurality of longitudinal strips 12 mounted to the proximal annular band 11; and a distal annular band 13, which is mounted to the distal ends of the longitudinal strips 12. Thus, the thigh module 20 has a basket appearance. The proximal annular band 11 is preferably attached to the thigh socket 2 of the prosthesis leg 1 using a Velcro fastener. The plurality of longitudinal strips 12 and the distal annular band 13 are preferably made of a plastic material, and may be formed as an integrated structure. The proximal annular band 11, the plurality of longitudinal strips 12 and the distal annular band 13 generally form the appearance of the thigh of a human leg, and constitute the thigh module 10. To adjust the length of the thigh module 10 according to the size of the patient, the longitudinal strips 12 are cut so that the length of the strips 12 is suitable for the patient, and, thereafter, the strips 12 are mounted to the proximal annular band 11. To adjust the length of the proximal annular band 11 according to the circumference of the thigh socket 2, several proximal annular bands 11 are prefabricated, and one of them is selected. When the prosthesis leg cover is modularized as described above, only limited kinds of modules, which have been prefabricated, can efficiently meet the requirements of many patients.

Figure 3:
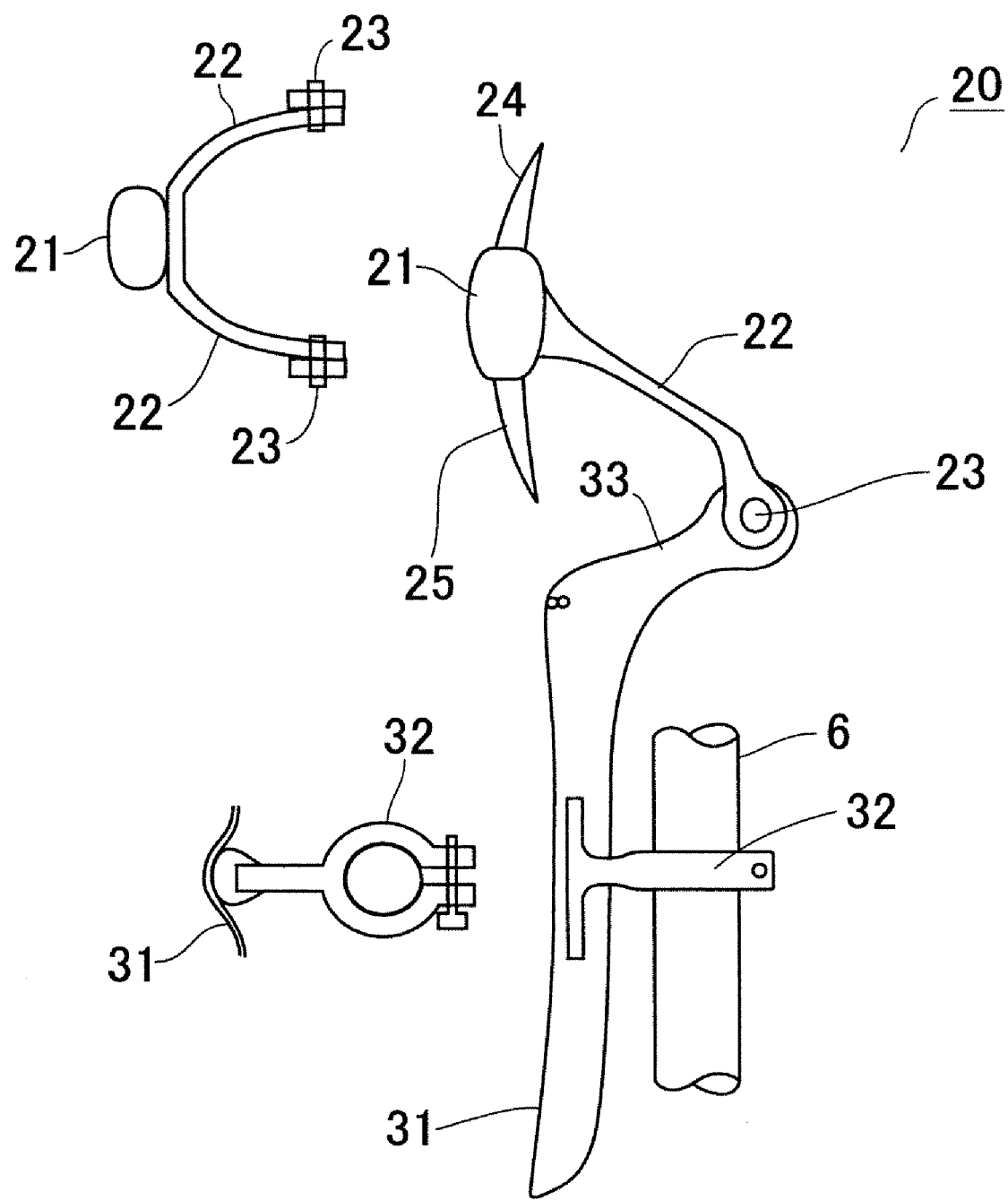
FIG. 3 illustrates parts of a patella module of the modularized prosthesis leg cover according to the present invention, in a plan view and a plan sectional view.

FIG. 3 illustrates the parts of the patella module 20 in a plan view and a plan sectional view. As shown in the drawing, the patella module 20 comprises: a patella part 21, a first stay part 33, and a second stay part 22. A tibia crest part 31 is secured to the lower leg pipe 6 of the prosthesis leg 1 using a fastener 32. The fastener 32 is integrated with the tibia crest part 31 using an adhesive. The tibia crest part 31 is preferably made of a hard plastic material. The upper part of the tibia crest part 31 is divided into two arms, and forms the first stay part 33, which extends backwards and upwards. The rear end of the first stay part 33 is provided with two stay shafts 23. The second stay part 22, which has a U-shape, is rotatably mounted to the rear end of the first stay part 33 by the two stay shafts 23. The second stay part 22 extends upwards and forwards, with the patella part 21 mounted to the upper end of the second stay part 22. In the present invention, the patella part 21 may be fixed to the second stay part 22, or may be mounted thereto so as to be rotatable to a small extent. The outer surface of the patella part 21 is provided with a thin elastic material. Further, a smooth fabric material is attached to the surface of the thin elastic material. Slightly soft pieces of plastic material are provided on the upper and lower ends of the patella part 21, thus forming a quadriceps femoris 24 and a patella tendon 25, respectively.

In the present invention, each of the stay shafts 23 is located at a predetermined position, which is lower than the knee joint shaft 5 of the prosthesis leg 1 and is adjacent to the knee joint of a real leg. When the stay shafts 23 are located as described above, the position of the patella part 21 can be appropriately adjusted by controlling the rotated position of the second stay part 22 around the stay shafts 23. Further, because the stay shafts 23, around which the patella part 21 is rotated, are located at a position that is lower than the knee joint shaft 5, as described above, when the knee joint part is bent, the patella part 21 is moved slightly backwards and is located in front of the central part of the bent knee joint part. Thus, the motion of the patella part 21 is similar to the motion of the patella of a real leg, and thus the location and appearance of the bent knee joint part of the prosthesis leg 1 are similar to those of a real leg.

As shown in FIG. 2, the lower leg module 30 comprises: the hard tibia crest part 31, which is securely fastened to the lower leg pipe 6 of the prosthesis leg 1 by the fastener 32; a soft calf part 34, which is attached to the tibia crest part 31 using an adhesive; and a calf front part 35. The calf part 34 is constructed by combining a pad, which is selected from among a variety of muscular soleus pads, with another pad, which is selected from a variety of muscular gastrocnemius pads. The respective pads of the calf part 34 are preferably made of a soft material, such as urethane foam. The shape and size of the calf front part 35 may be changed according to the selected foot part, and thus it is required that a prosthesis leg manufacturer specifically produce the calf front part 35, and that a prefabricated product not be used.

Figure 4:
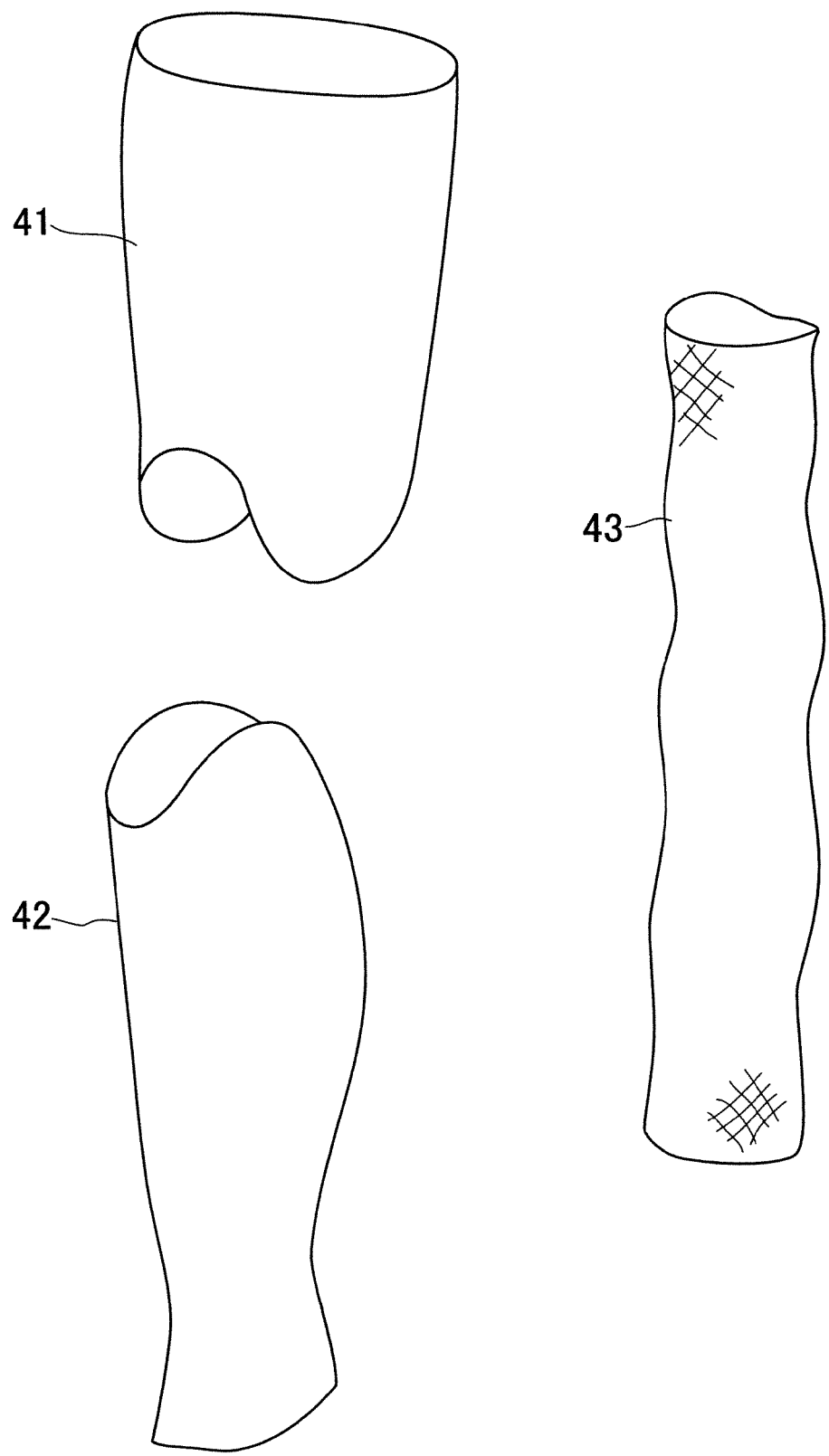
FIG. 4 is an exploded perspective view illustrating a skin module of the modularized prosthesis leg cover according to the present invention.

FIG. 4 is an exploded perspective view illustrating a skin module of the present invention. The basket-shaped thigh module 10 is covered with a thigh shell 41, and the lower leg module 30 is covered with a calf shell 42. Each of the two shells 41 and 42 is preferably made of a soft material to form a shell body having a thickness of about 5 mm. A skin module 43, which comprises contractible tights made of a stretchable fiber, covers the two shells 41 and 42, and forms the prosthesis leg cover of the present invention. In the present invention, the skin module 43 accomplishes the alignment of the two shells 41 and 42. Further, the skin module 43 comes into contact with and compresses the patella part 21 of the patella module 20. Thus, in response to bending motion of the knee joint part, the skin module 43 rotates the second stay part 22 and thus guides the patella part 21 to an appropriate location. Therefore, when the patient bends and stretches the knee joint part of the prosthesis leg, the patella part 21 executes a smooth motion, which is similar to that of a real leg.

In the prosthesis leg cover, the kneecap is configured as an independent part, which is formed by the patella module 20, so that the front surface of the knee joint part of the prosthesis leg avoids damage despite undergoing repeated bending motions. Further, when the patient bends and stretches the knee joint part, the patella part 21 executes a smooth motion and forms a realistic shape, which is similar to that of a real leg.

The prosthesis leg cover of the present invention can be provided to a patient as follows. The calf front part 35 must be specifically produced to fit the patient. However, the other parts 11, 12, 21, 22, 31 and 34 of the modules 10, 20 and 30 can be provided as prefabricated parts, and different sizes and shapes can be made available for each part. Some suitable parts are selected from among the prefabricated parts according to the characteristics of the patient, and are assembled with each other, together with the specifically produced calf front part 35, thus forming respective modules 10, 20 and 30. Thereafter, the modules are assembled together to form a desired prosthesis leg cover that fits the patient. Thus, the time period required to produce the prosthesis leg cover and provide it to the patient can be greatly reduced. Further, when one of the parts is damaged or broken, it can be quickly and simply changed with a new part, so that it is possible to quickly and easily repair the prosthesis leg cover.

Figure 5:
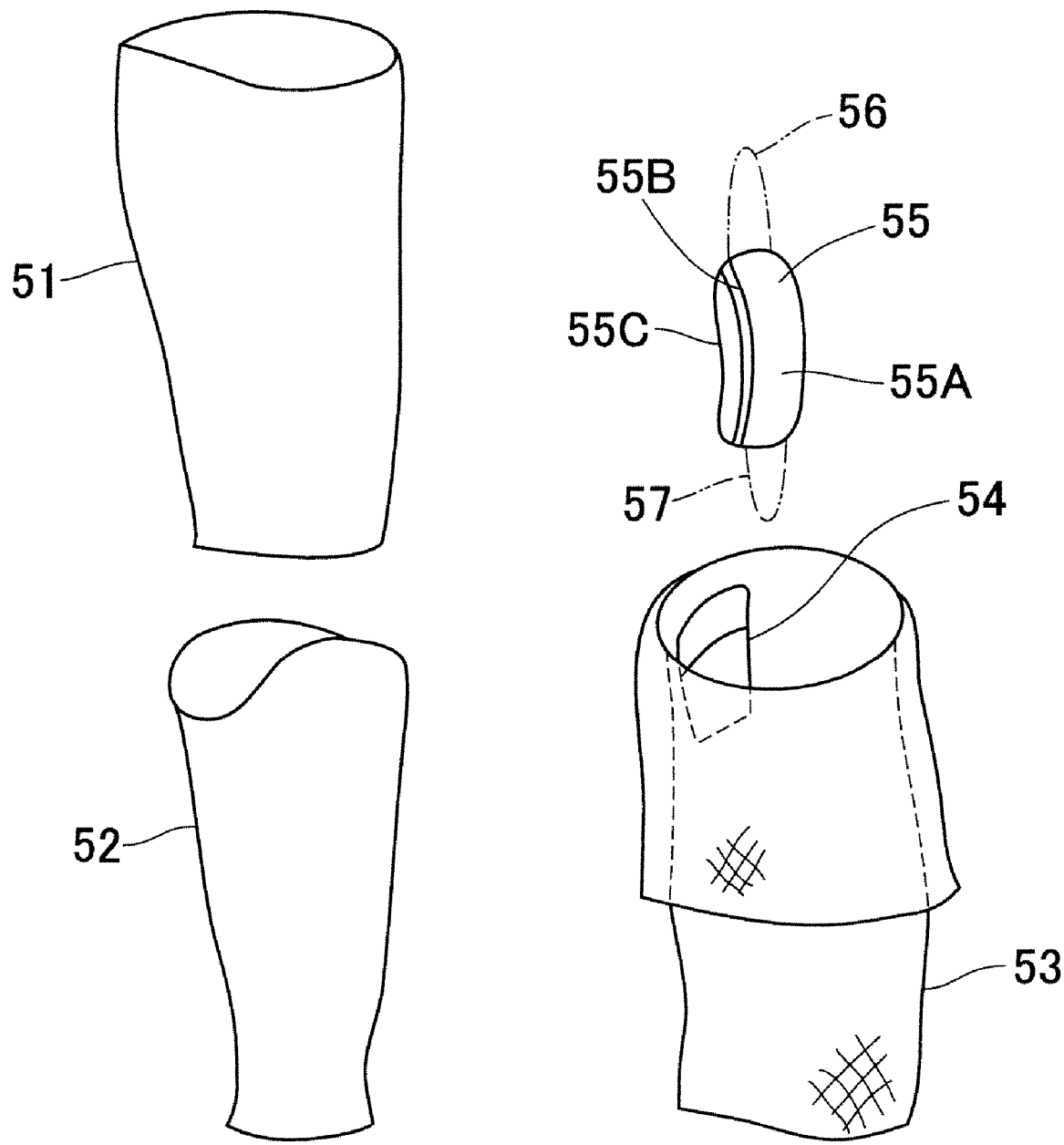
FIG. 5 is an exploded perspective view illustrating a skin module according to a second embodiment of the present invention, which functions as a support in place of a stay, for supporting a patella part.

FIG. 5 is an exploded perspective view illustrating a skin module according to a second embodiment of the present invention, which functions as a support, instead of the stay, for supporting a patella part. In this embodiment, the skin module 53 covers both a thigh shell 51 and a lower leg shell 52. The skin module 53 comprises contractible tights made of a stretchable fiber. FIG. 5 shows that the skin module 53 is folded down at the kneecap. The skin module 53 is provided with an inside pocket 54, which has a lid flap and is provided on the rear portion of the skin module 53 at a position diametrically opposite the knee joint part. The inside pocket 54 receives a patella part 55 therein. The patella part 55 comprises: a hard resin layer 55A, which is made of a hard synthetic resin and forms a rear layer of the patella part 55; a soft middle layer 55B, which is made of soft urethane foam; and a leather layer 55C, which forms an outside layer of the patella part 55. When the patella part 55 is configured as the triple-layered structure as described above, the patella part 55 becomes similar to the knee of a real leg, and thus can be comfortable for the patient. In this embodiment, the patella module comprises only the patella part 55. Further, the patella part 55 is preferably provided with upper and lower bands 56 and 57, such that the upper and lower bands 56 and 57 protrude outside the inside pocket 54.

The above-mentioned second embodiment of the skin module 53 is advantageous as follows. 1) The patella module comprises only the patella part 55, so that the patella module has a reduced number of parts and thus productivity is increased. 2) A prosthesis leg manufacturer can easily produce the patella module. 3) A variety of knee joint parts can be used with the patella module without limit. 4) The knee joint part has a realistic shape similar to the shape of a real leg. 5) The patella module can be easily and simply changed with a new one. 6) When the patella module is provided with the upper and lower bands, it is possible to reliably prevent the undesired leftward and rightward movement of the patella module.

Figure 6:
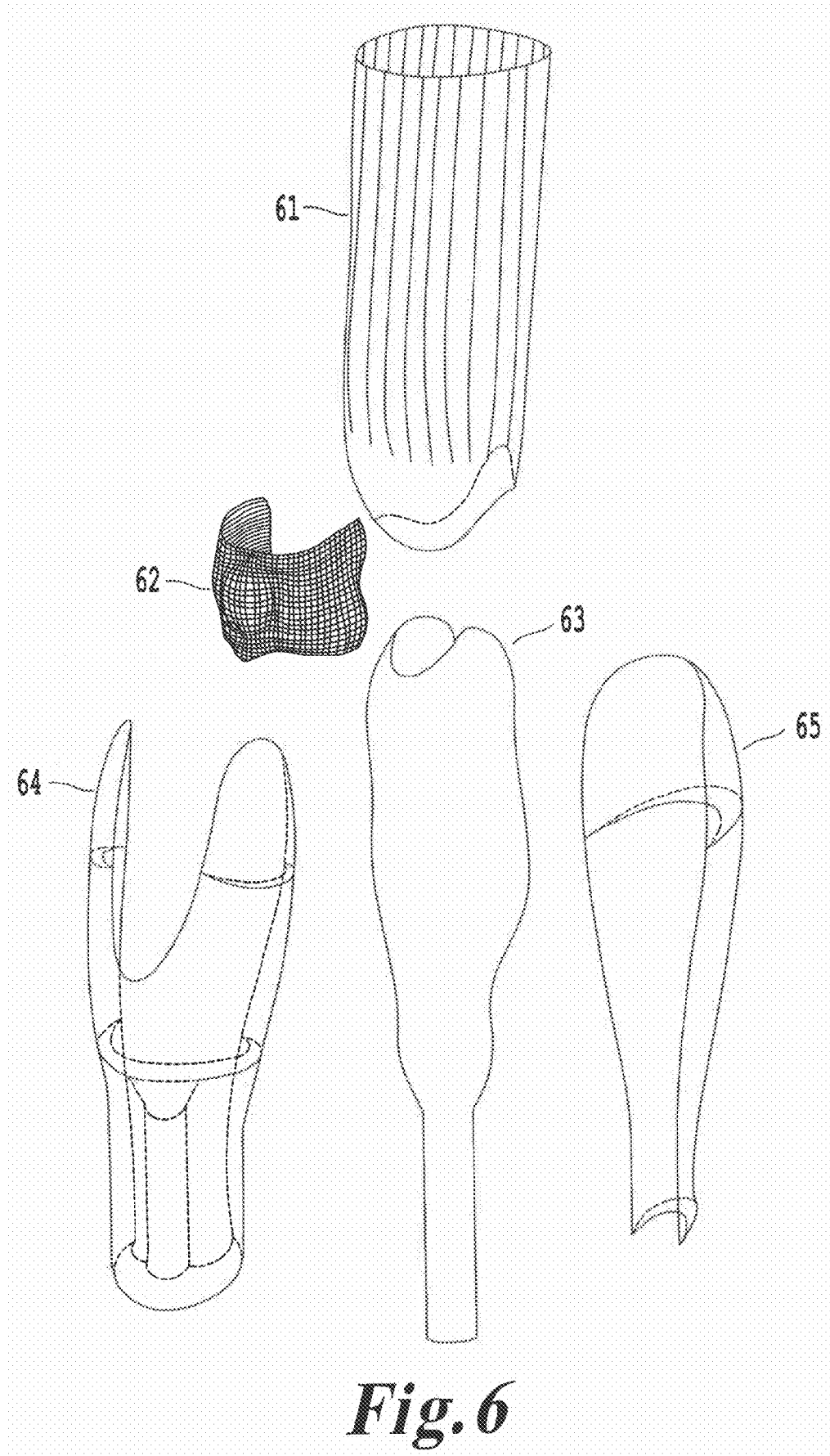
FIG. 6 is a perspective view illustrating a prosthesis leg cover according to a third embodiment of the present invention.

FIG. 6 is a perspective view illustrating a prosthesis leg cover according to a third embodiment of the present invention. As shown in the drawing, the prosthesis leg cover according to the third embodiment comprises a thigh module 61, a patella module 62 and a lower leg module 63. The lower leg module 63 is provided with a lower leg front pad 64 and a lower leg rear pad 65, thus forming a lower leg part. The thigh module 61 comprises a plurality of pieces and is formed through a polyethylene blow molding process. The patella module 62 is made of EVA (ethylene vinyl acetate copolymer), which is a resin similar to rubber, so that the patella module 62 has a kneecap shape. The lower leg module 63 is made of polyethylene to form a body having a thickness of about 1 mm through a blow molding process. The lower leg front pad 64 is made of polyethylene foam, and forms a shin part. The lower leg rear pad 65 is made of polyethylene foam and forms the calf part. The thigh module 61, the patella module 62 and the lower leg module 63 are assembled with each other to form a basic body of the prosthesis leg cover, and, thereafter, both the lower leg front pad 64 and the lower leg rear pad 65 are attached to the lower leg module 63, thus completely forming a lower leg shell of the prosthesis leg cover of the present invention.

Figure 7:
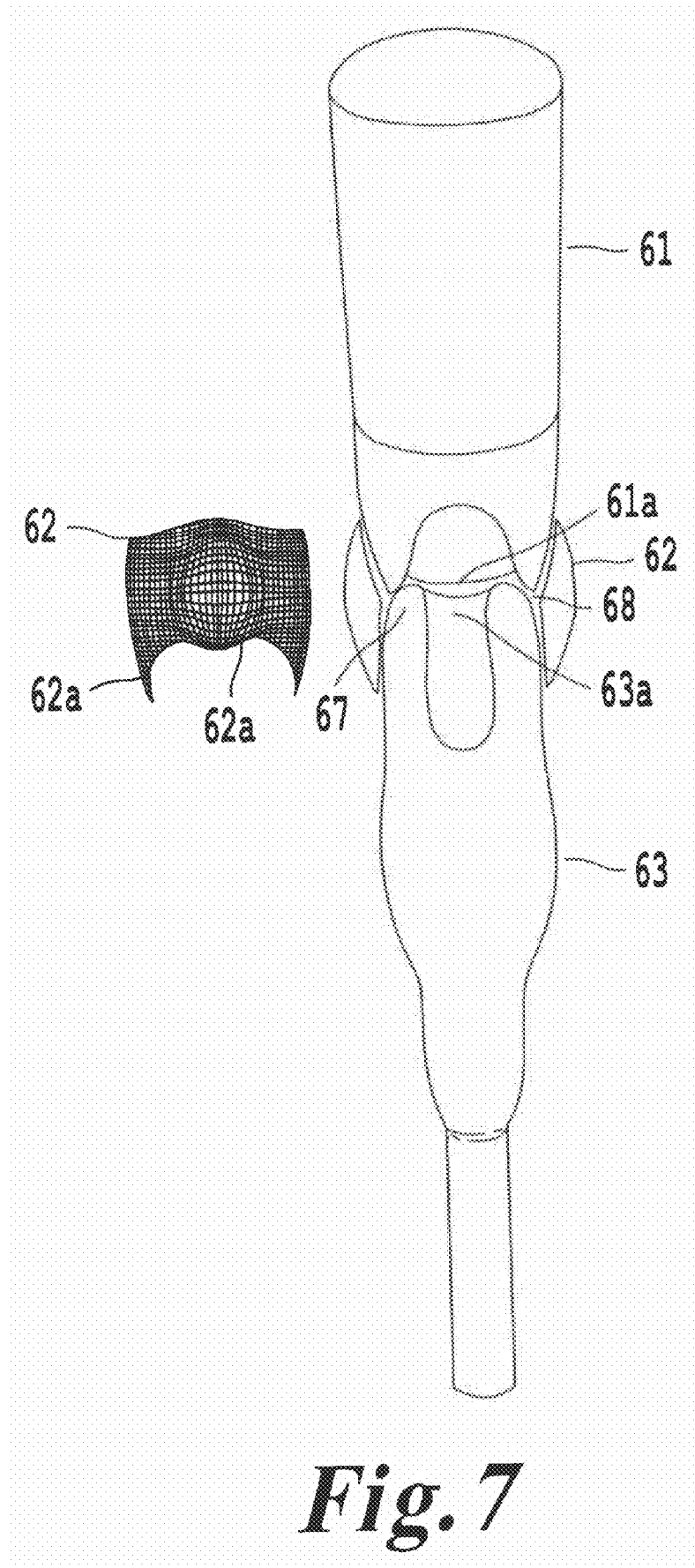
FIG. 7 is a rearview illustrating the prosthesis leg cover of the third embodiment of the present invention.

FIG. 7 is a rearview illustrating the prosthesis leg cover of the third embodiment of the present invention. In FIG. 7, the lower leg front pad 64 and the lower leg rear pad 65 are not shown. When the thigh module 61, the patella module 62 and the lower leg module 63 are assembled with each other to form a prosthesis leg cover, two protrusions 62a, which are formed on opposite sides of the rear part of the patella module 62, are inserted into respective grooves 67 and 68, which are provided between a lower round surface 61a of the thigh module 61 and an upper round surface 63a of the lower leg module 63 and are formed from the front part to the opposite sides of the knee joint part. Due to the engagement of the two protrusions 62a with the respective grooves 67 and 68, the location of the patella module 62 can be more reliably set. Thus, the patella module 62 can execute a motion similar to that of a real leg.

Figure 8:
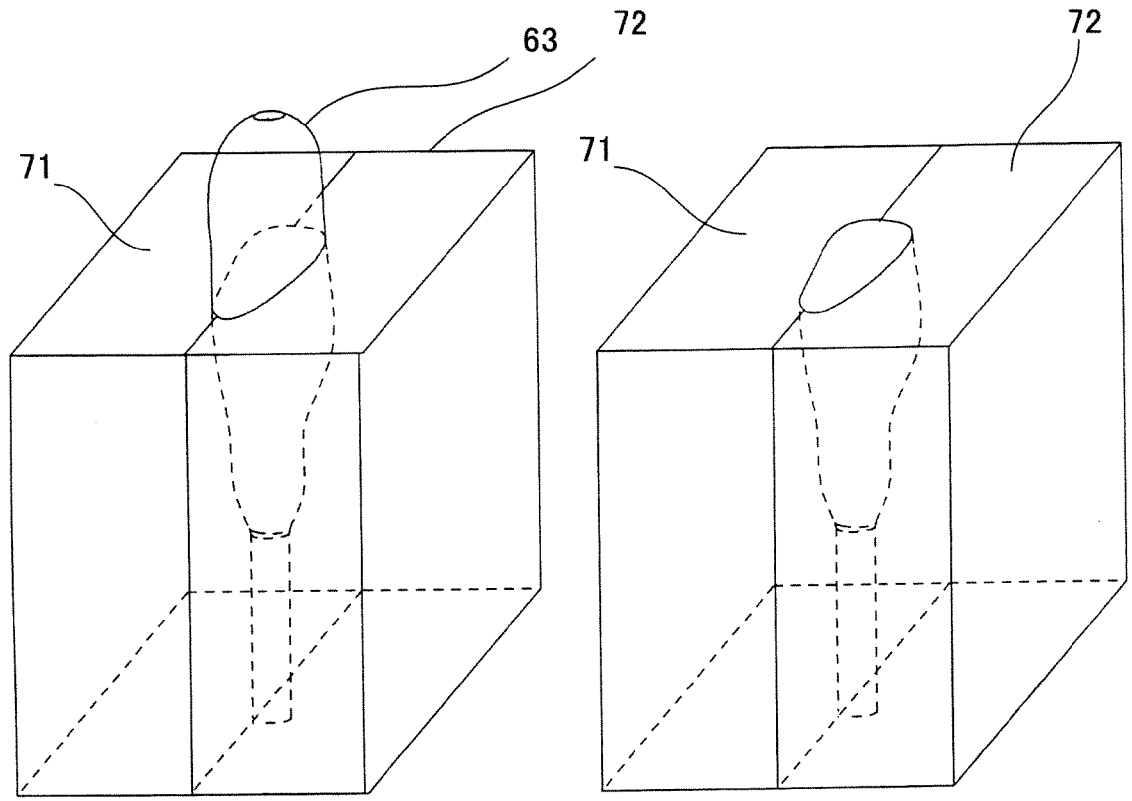
FIG. 8 is a perspective view illustrating a process for manufacturing a lower leg left-side pad and a lower leg right-side pad according to a fourth embodiment of the present invention.
Figure 8:
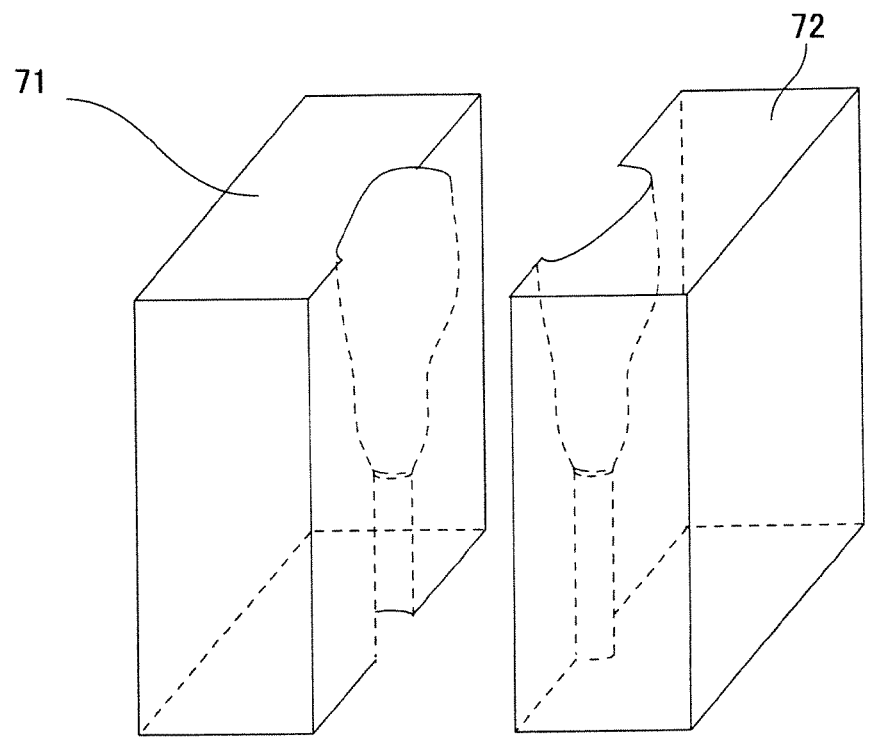

FIG. 8 is a perspective view illustrating a process for manufacturing a lower leg left-side pad and a lower leg right-side pad according to a fourth embodiment of the present invention. As shown in the drawing, to precisely form the lower part of the lower leg module 63, both a left-side pad block 71 and a right-side pad block 72, which can receive part of the lower leg module 63 therein, are prepared by cutting two rectangular blocks to form grooves in the respective blocks 71 and 72. The respective pad blocks 71 and 72 are preferably made of polyethylene foam. A prosthesis leg manufacturer cuts the left-side pad block 71 and the right-side pad block 72 to fit a patient, thus forming a desired shape of the lower leg part, which fits the patient. The left-side pad block 71 and the right-side pad block 72, which have been cut to fit the patient, are attached to the lower leg module 63, thus forming a prosthesis leg cover. The left-side pad block 71 forms the lower leg first pad, while the right-side pad block 72 forms the lower leg second pad. In the present invention, the lower leg pad may be divided into the front pad and the rear pad, or may be divided into the left-side pad and the right-side pad, as described above. Further, the lower leg first pad and the lower leg second pad may be integrally formed as a single structure.

Figure 9:
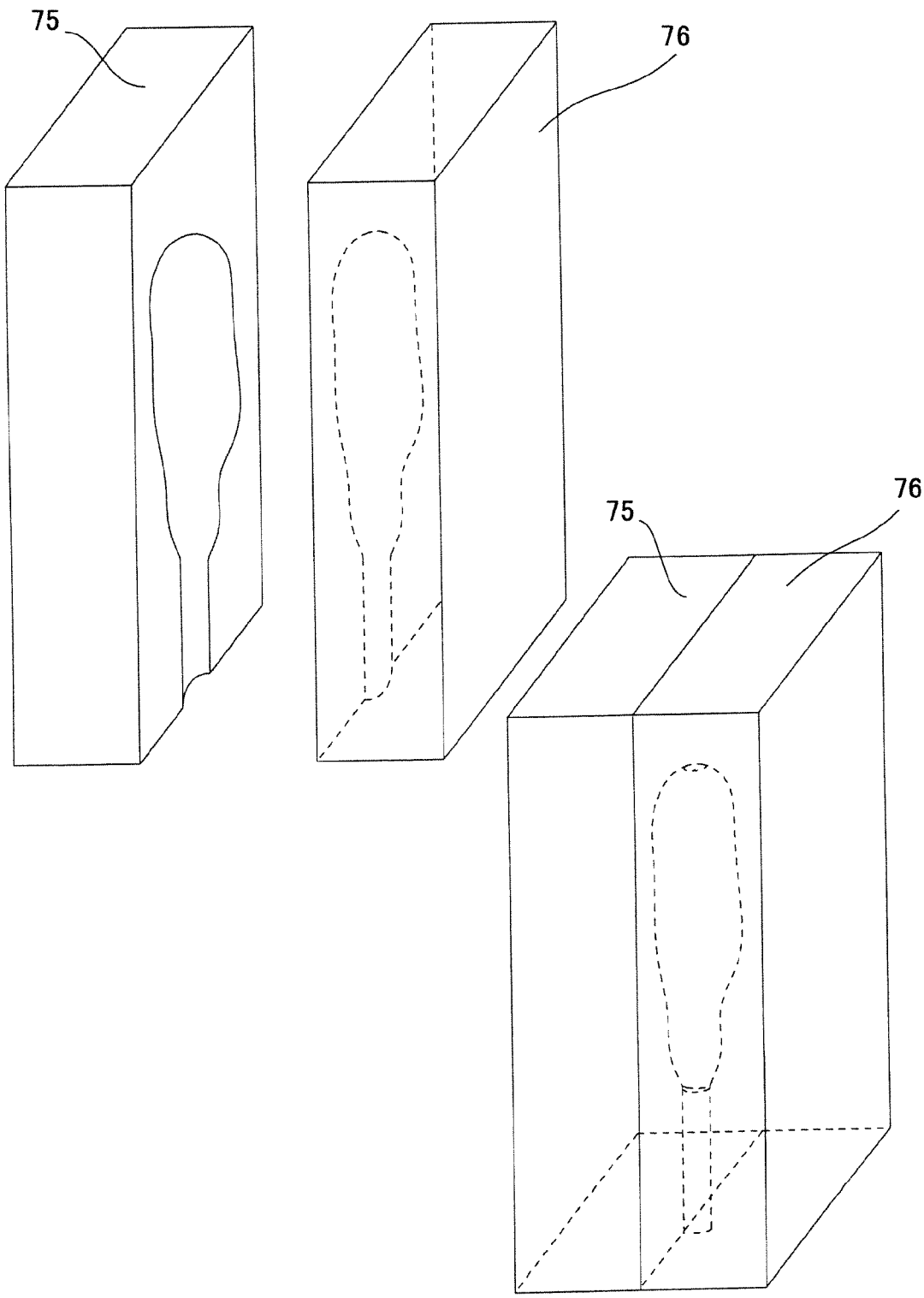
FIG. 9 is a perspective view illustrating a process for manufacturing a lower leg left-side pad and a lower leg right-side pad according to a fifth embodiment of the present invention.

FIG. 9 is a perspective view illustrating a process for manufacturing a lower leg left-side pad and a lower leg right-side pad according to a fifth embodiment of the present invention. As shown in the drawing, unlike the fourth embodiment of FIG. 8, a rectangular left-side pad block 75 and a rectangular right-side pad block 76, which can receive the entire lower leg module 63 therein, are provided in this fifth embodiment, however, the other parts of the pad blocks 75 and 76 of this fifth embodiment remain the same as those of the embodiment of FIG. 8. For a description of parts that are not different from the fourth embodiment of FIG. 8, reference may be made to the description for the embodiment of FIG. 8. The respective pad blocks 75 and 76 are preferably made of polyethylene foam.

Figure 10:
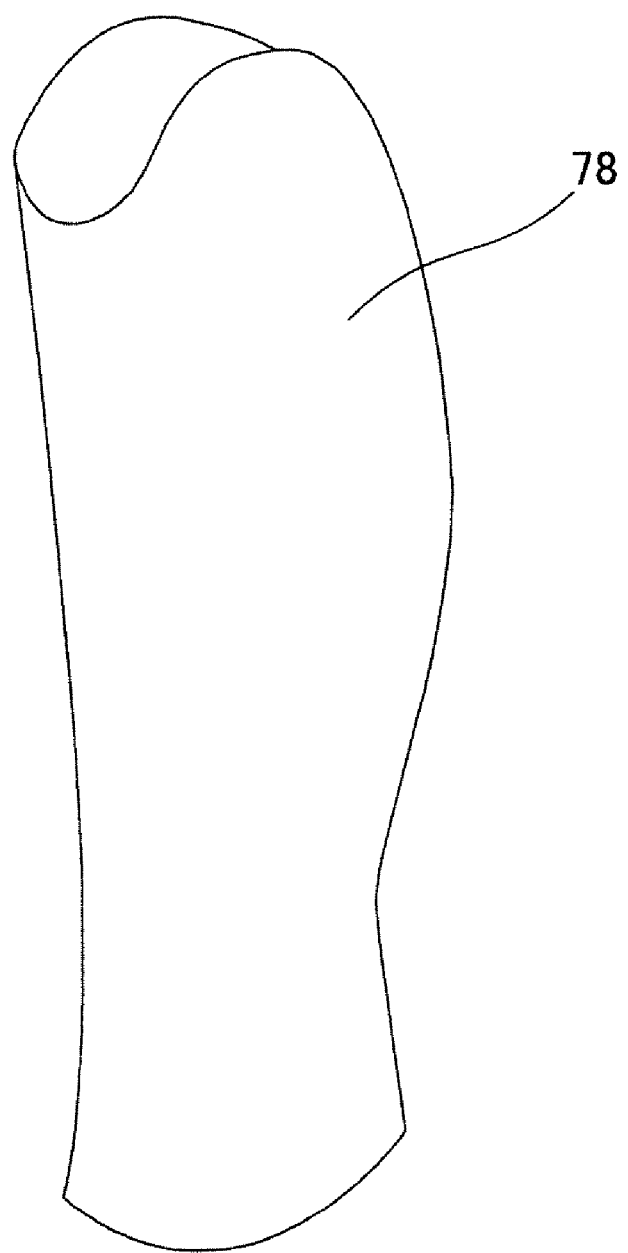
FIG. 10 is a perspective view illustrating a lower leg first pad and a lower leg second pad according to a sixth embodiment of the present invention.

FIG. 10 is a perspective view illustrating a lower leg first pad of and a lower leg second pad according to a sixth embodiment of the present invention. As shown in the drawing, in this embodiment, a sheet of material is rolled to form a lower leg part having a desired cylindrical shape, thus forming a lower leg pad 78 without cutting a block to form the lower leg pad. In this embodiment, the lower leg first pad and the lower leg second pad are integrally formed as a single structure. Examples of the sheet material are sponge sheets, resin sheets, EVA sponge sheets, polyethylene foam sheets, neoprene sheets, etc. The cylindrically rolled lower leg pad 78 covers the lower leg module 63.

Figure 11:
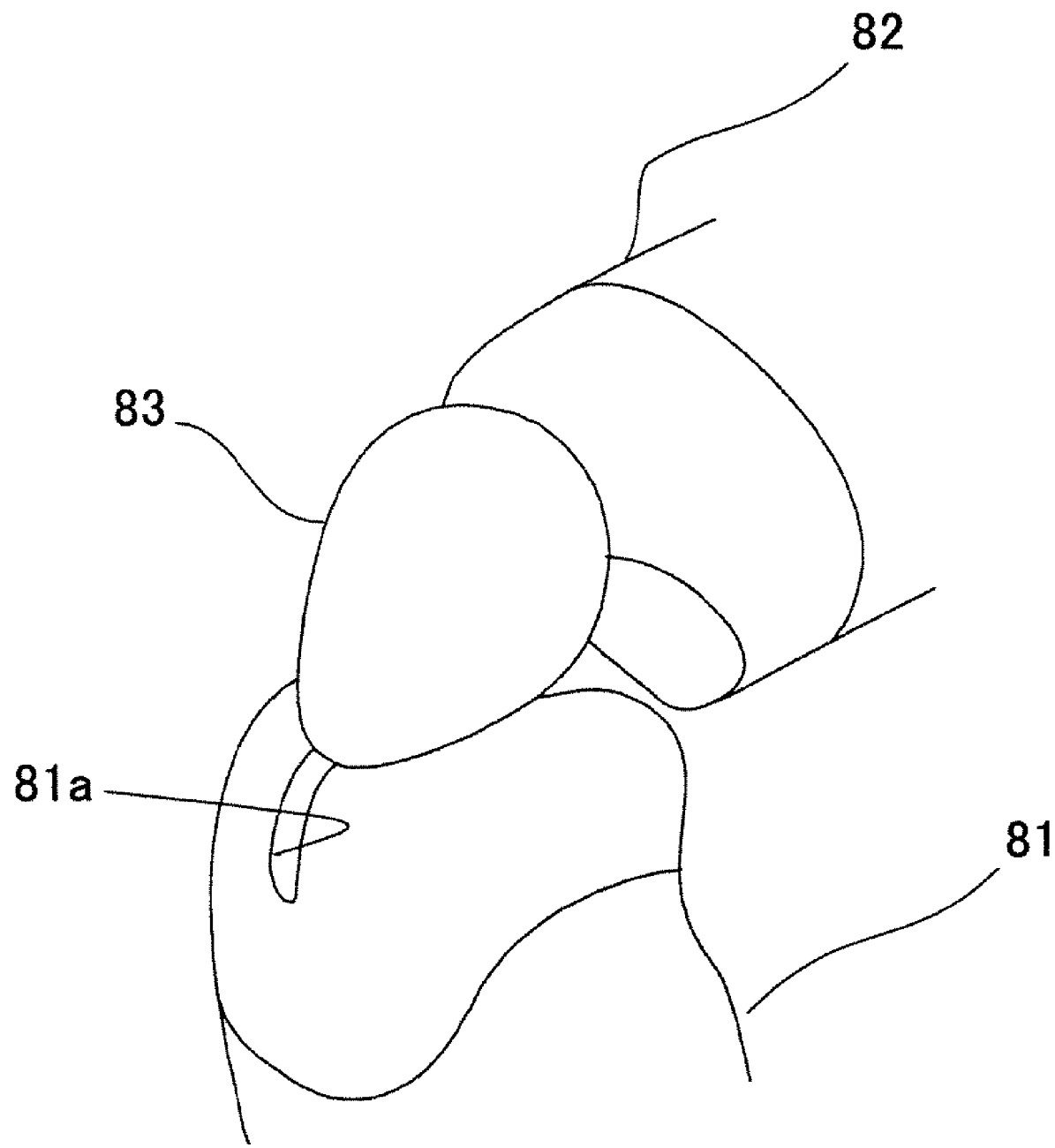
FIG. 11 is a perspective view illustrating a patella module according to a fourth embodiment of the present invention.

FIG. 11 is a perspective view illustrating a patella module according to a fourth embodiment of the present invention. The first embodiment, the second embodiment and the third embodiment of the patella module are shown in FIG. 3, FIG. 5 and FIG. 6, respectively. In the fourth embodiment, a patella module 83 is placed between a lower leg module 81 and a thigh module 82. A longitudinal guide slit 81a is formed in the lower leg module 81, so that the movement of the patella module 83 is guided by the guide slit 81a.

Figure 12:
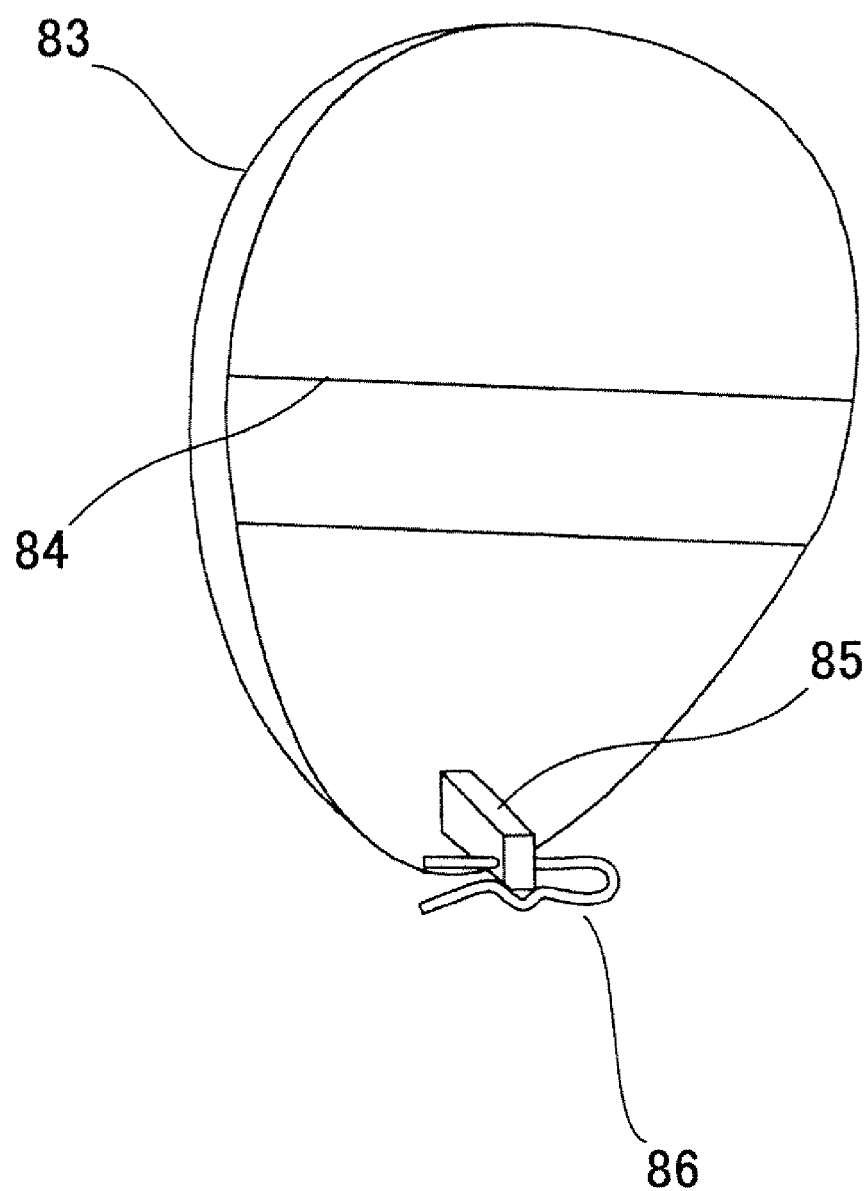
FIG. 12 is a rear perspective view of the patella module of FIG. 11.

FIG. 12 is a rear perspective view of the patella module of FIG. 11. As shown in the drawing, a rubber band 84 extends horizontally along the central part of the patella module 83. A protrusion 85 is provided on the lower part of the patella module 83, and a stop pin 86 is provided on the protrusion 85. When the patella module 83 is assembled with the lower leg module 81, the protrusion 85 of the patella module 83 is inserted into the guide slit 81a of the lower leg module 81 and is locked inside the lower leg module 81 by the stop pin 86. Thus, the protrusion 85 can be moved under the guidance of the guide slit 81a, so that the patella part 83 can be moved in response to bending motion of the knee joint part. The rubber band 84 functions to prevent the patella part 83 from being undesirably inserted into the gap between the lower round surface 61a of the thigh module 61 and the upper round surface 63a of the lower leg module 63 during a bending motion of the knee joint part. In the above state, the patella module 83 is stably moved.

Figure 13:
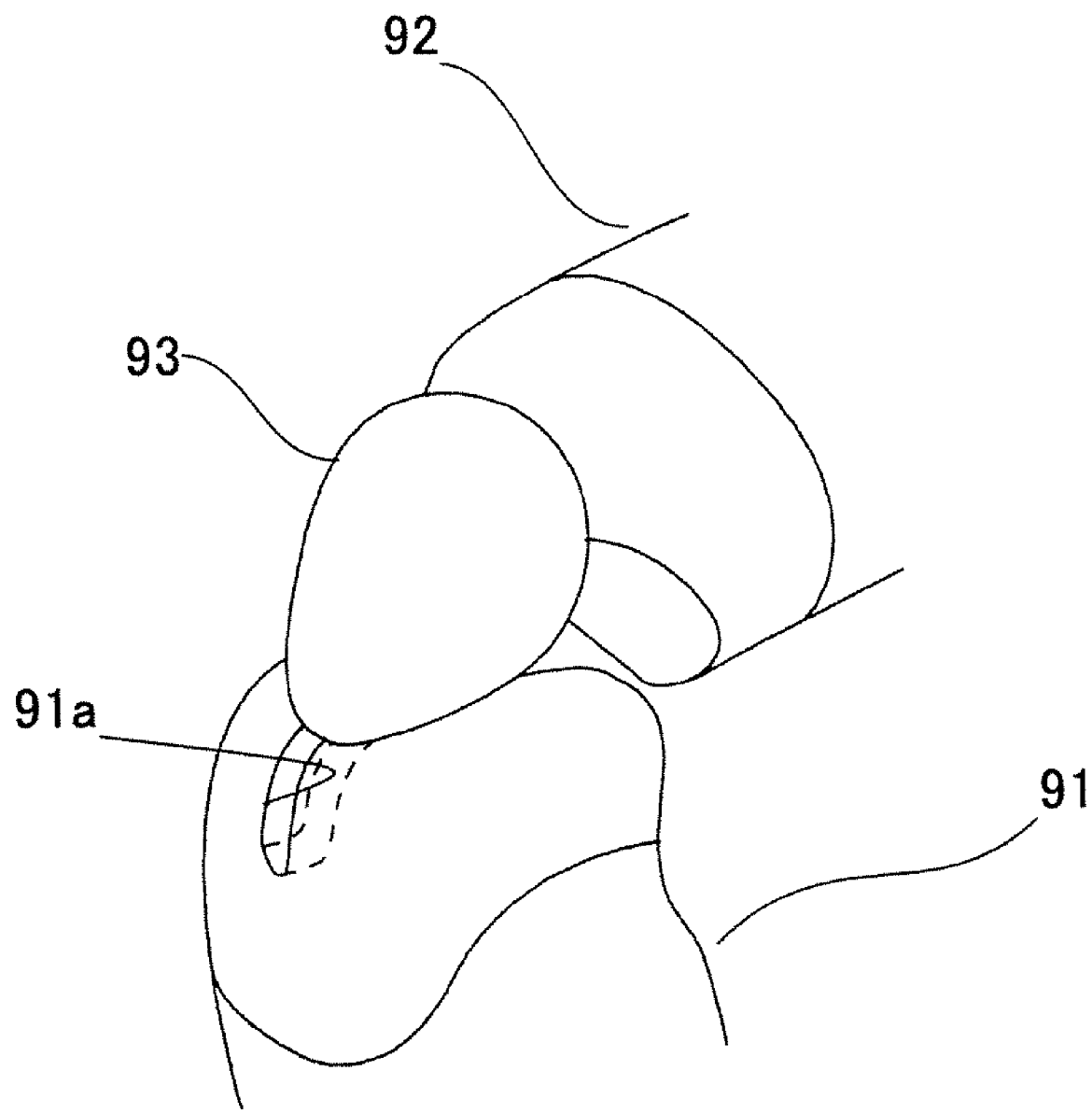
FIG. 13 is a perspective view illustrating a patella module according to a fifth embodiment of the present invention.

FIG. 13 is a perspective view illustrating a patella module according to a fifth embodiment of the present invention. In this embodiment, a patella module 93 is placed between a lower leg module 91 and a thigh module 92. A longitudinal guide slit 91a is formed in the lower leg module 91, while the patella module 91 is moved under the guidance of the guide slit 91a.

Figure 14:
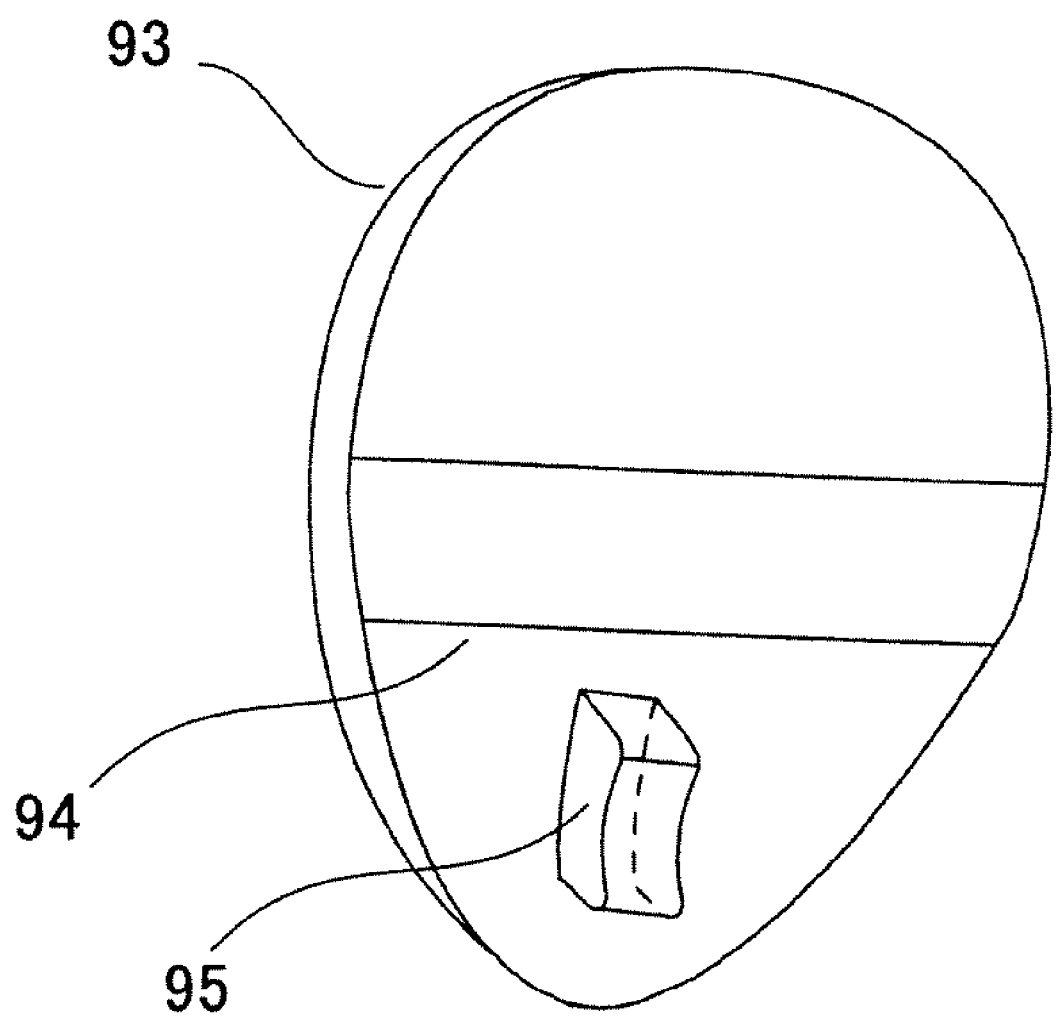
FIG. 14 is a rear perspective view of the patella module of FIG. 13.

FIG. 14 is a rear perspective view of the patella module of FIG. 13. As shown in the drawing, a rubber band 94 extends horizontally along the central part of the patella module 93. A protrusion 95 is provided on the lower part of the patella module 93. The end surface of the protrusion 95 is curved to meet the round shape of the lower part of the guide slit 91a, so that the patella module 93 can be assembled with the lower leg module 91 simply by inserting the protrusion 95 into the guide slit 91a. Thus, the patella module 93 can be moved under the guidance of the guide slit 91a. Unlike the fourth embodiment, in this fifth embodiment, the patella module 93 is not mechanically assembled with the lower leg module 91, so that, when the patient repeatedly bends the knee joint part, the patella module 93 does not become damaged or broken.

Figure 15:
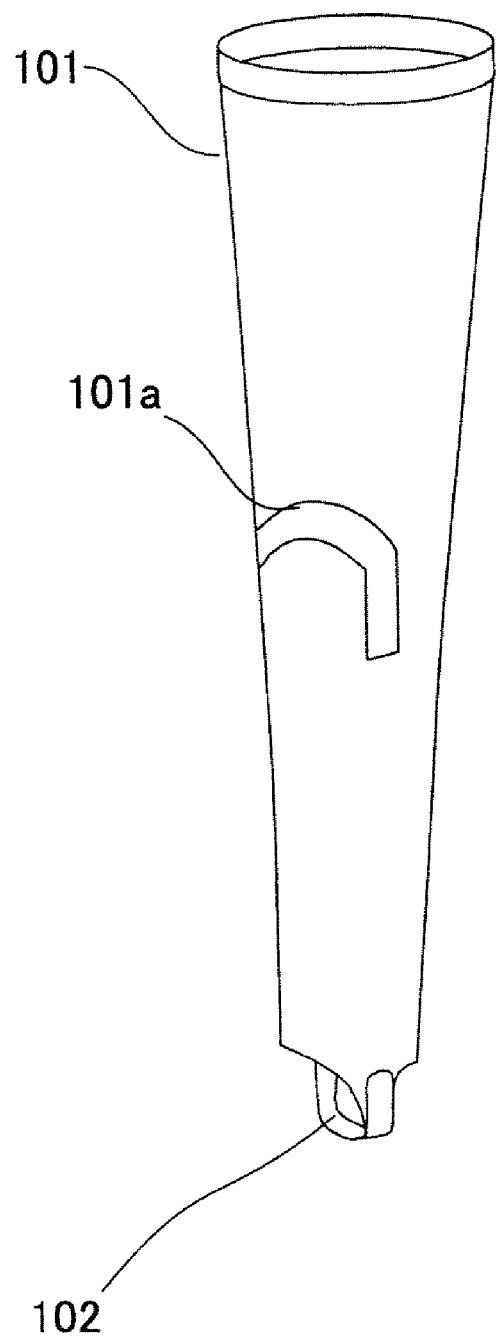
FIG. 15 is a perspective view illustrating a skin module according to a third embodiment of the present invention.
Figure 16:
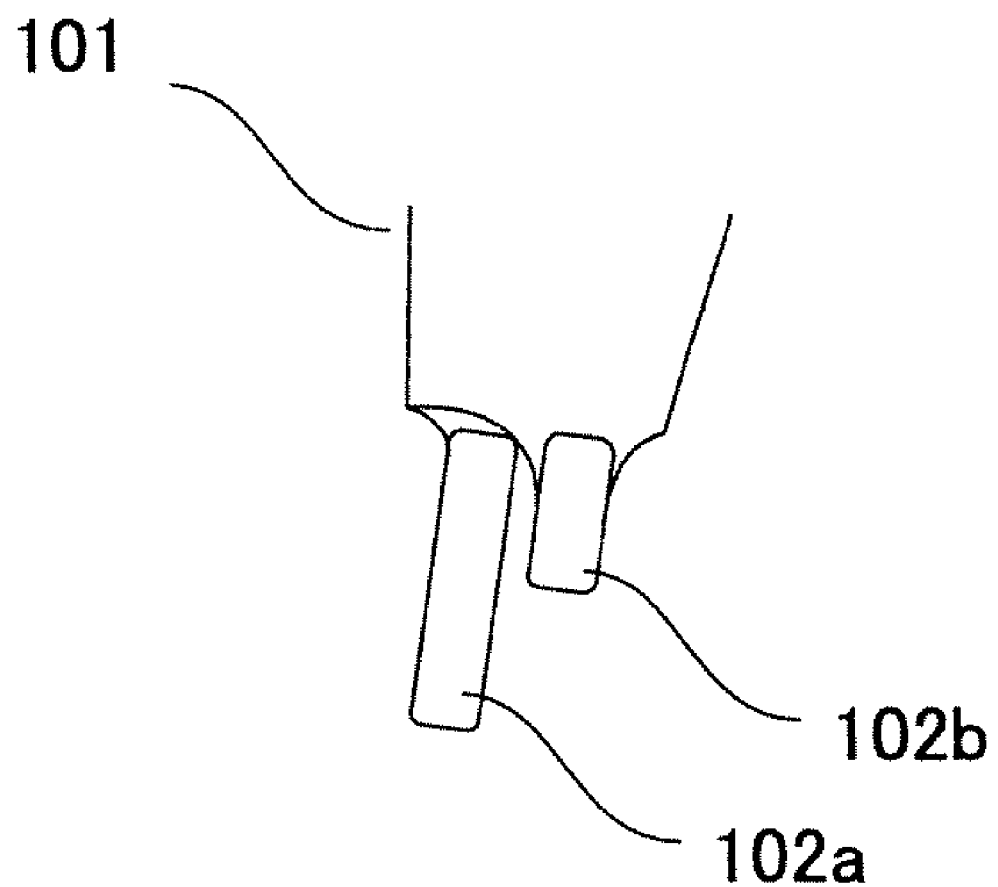
FIG. 16 is a perspective view illustrating the distal end of the skin module of FIG. 15.
Figure 17:
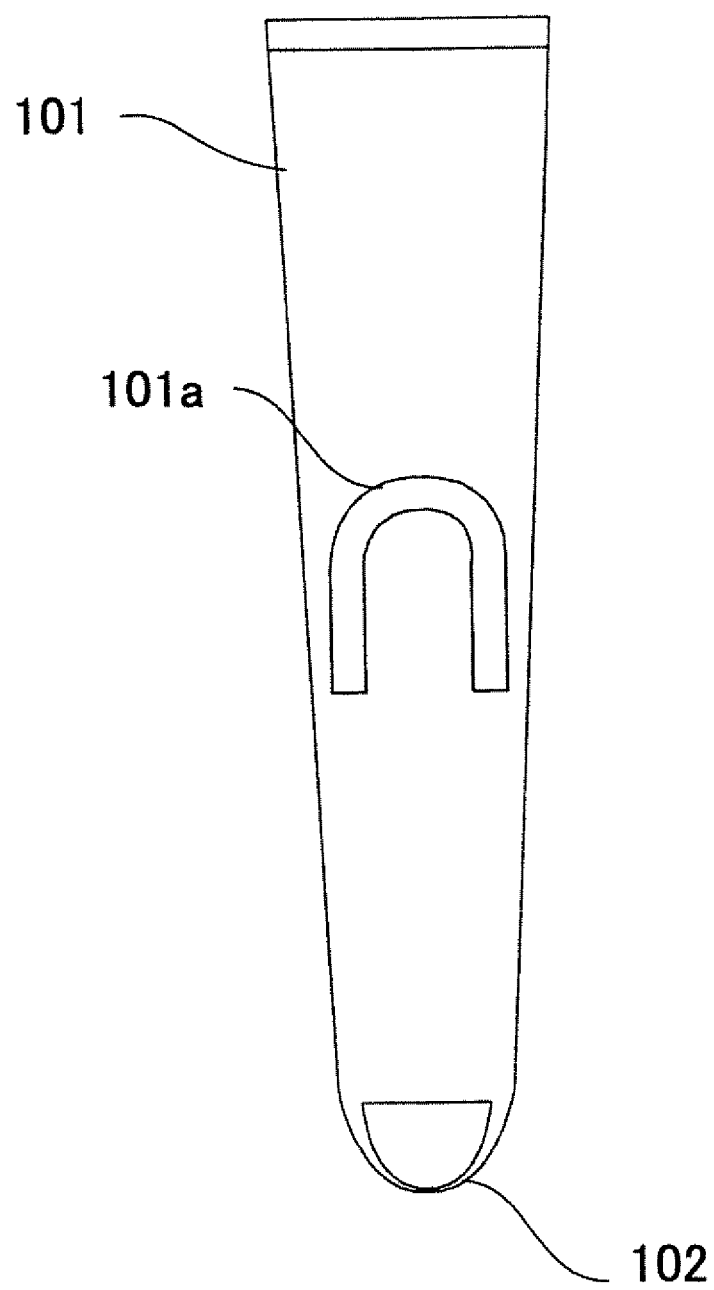
FIG. 17 is a front view illustrating the skin module of FIG. 15.
Figure 18:
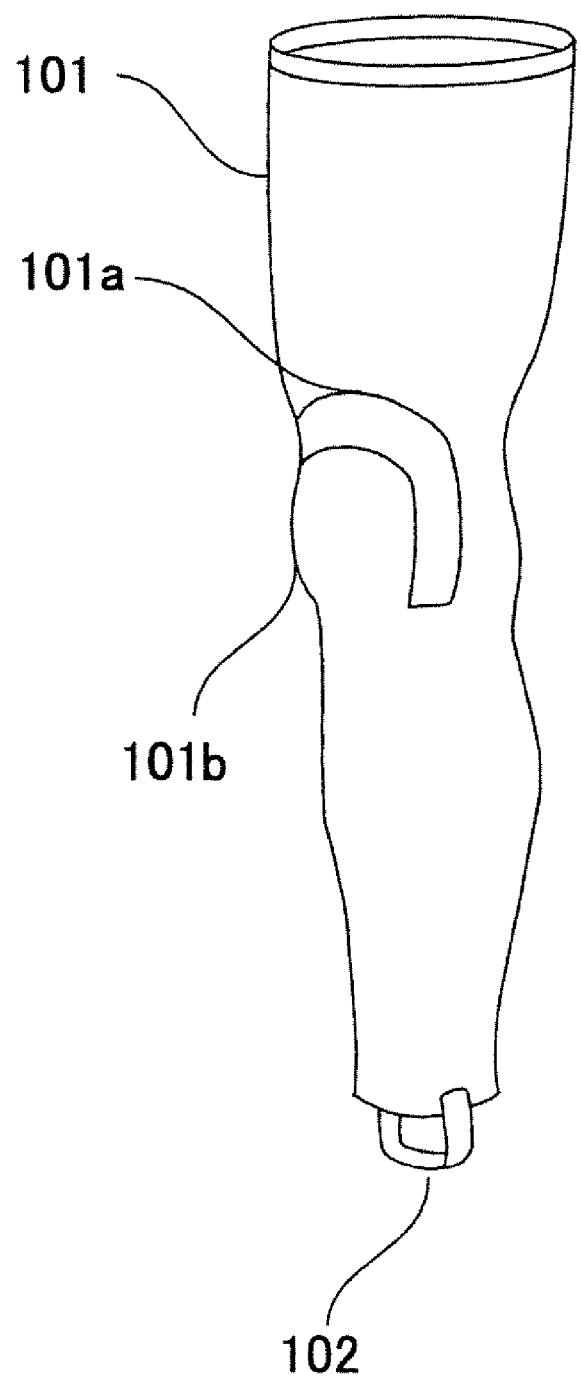
FIG. 18 is a perspective view illustrating the skin module of FIG. 15, which covers the prosthesis leg cover of the present invention.

FIG. 15 is a perspective view illustrating a skin module according to a third embodiment of the present invention. The skin module 101 of this embodiment is preferably made of a stretchable fiber, such as a fiber used for making stockings or tights. According to the direction in which the fiber is knit to produce the skin module 101, the contractibility of the skin module 101 varies such that a reverse U-shaped knitted part 101a has high contractibility and the other knitted parts of the skin module 101 have low contractibility. A stirrup 102 is provided at the lower end of the skin module 101. The stirrup 102 may comprise two parts 102a and 102b, as shown in FIG. 16, with the opposing pieces of a Velcro fastener attached to the two respective parts 102a and 102b, so that the size of the stirrup 102 can be adjusted. FIG. 17 is a front view illustrating the skin module of FIG. 15. The reverse U-shaped knitted part 101a, which has high contractibility, is located at a position corresponding to the kneecap. To wear the prosthesis leg cover of the present invention, the thigh module, the patella module and the lower leg module of the prosthesis leg cover are attached to an endoskeletal prosthesis leg, and, thereafter, the prosthesis leg cover may be covered with the lower leg front pad 64 and the lower leg rear pad 65. Alternatively, as shown in FIG. 8 and FIG. 9, the prosthesis leg cover may be covered with the lower leg first pad and the lower leg second pad, which have been produced using the pad blocks. As a further alternative, the prosthesis leg cover may be covered with the lower leg pad 78 of FIG. 10. Thereafter, the pads of the prosthesis leg cover are covered with the skin module 101 of FIG. 15. FIG. 18 is a perspective view illustrating the skin module 101 of FIG. 15, which covers the prosthesis leg cover of the present invention. As shown in the drawing, the patella module forms a bulged part 101b on the skin module 101 at a position corresponding to the kneecap. Further, the reverse U-shaped knitted part 101a, which has high contractibility, is located so that it surrounds the bulged part 101b. In response to bending motion of the knee joint part, the reverse U-shaped knitted part 101a, which has high contractibility, limits the movement of the patella module.

While the invention has been shown and described with respect to the preferred embodiments, it will be understood by those skilled in the art that various changes and modifications may be made without departing from the spirit and scope of the invention as defined in the following claims.

What is claimed is:

1. A modularized prosthesis leg cover, comprising:
a thigh cover module mountable to a prosthesis leg at a position above a knee joint part, the thigh cover module forming a thigh shell for the prosthesis leg;
a patella module forming a kneecap for the prosthesis leg;
a lower leg cover module mountable to the prosthesis leg at a position below the knee joint part, the lower leg cover module forming a lower leg part for the prosthesis leg;
a lower leg front pad and a lower leg rear pad mounted to the lower leg cover module, the lower leg front and rear pads forming a lower leg shell; and
a skin module covering the thigh cover module, the patella module, the lower leg front pad, and the lower leg rear pad, wherein
the thigh cover module, the patella module, and the lower leg cover module are separately assembled to each other,
the prosthesis leg cover is a shell for covering the prosthesis leg, and
the skin module is provided with a contractible reverse U-shaped knitted part at a position corresponding to the kneecap.
wherein the patella module includes two protrusions formed on opposite sides of a rear part of the patella module, and grooves are formed between a lower round surface of the thigh cover module and an upper round surface of the lower leg cover module such that the protrusions of the patella module fit into respective ones of the grooves.

2. The modularized prosthesis leg cover as claimed in claim 1, wherein the skin module is made of a stretchable fiber.

3. The modularized prosthesis leg cover as claimed in claim 1, wherein the patella module has a shape of a human kneecap.

* * * * *